(12) United States Patent
Kan et al.

(10) Patent No.: US 8,003,380 B2
(45) Date of Patent: Aug. 23, 2011

(54) HIGH THROUGHPUT CELL-BASED ASSAYS FABRICATED WITH INTEGRATED SILICON AND CELL CULTURE TECHNOLOGIES

(75) Inventors: Shyi Herng Kan, Singapore (SG); Jackie Y. Ying, Singapore (SG); Henry Yu, Singapore (SG); Karl Schumacher, Singapore (SG); Susanne San San Ng, Singapore (SG); Wanxin Sun, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 1569 days.

(21) Appl. No.: 11/325,609

(22) Filed: Jan. 4, 2006

(65) Prior Publication Data
US 2007/0155007 A1 Jul. 5, 2007

(51) Int. Cl.
*C12M 1/12* (2006.01)
(52) U.S. Cl. .................................................. 435/297.1
(58) Field of Classification Search ............... 435/297.1
See application file for complete search history.

(56) References Cited

U.S. PATENT DOCUMENTS

| | | | |
|---|---|---|---|
| 5,380,536 A | 1/1995 | Hubbell et al. | |
| 5,514,378 A | 5/1996 | Mikos et al. | |
| 6,676,675 B2 | 1/2004 | Mallapragada et al. | |
| 6,787,358 B2 | 9/2004 | Nelles et al. | |
| 6,942,873 B2 | 9/2005 | Russell et al. | |
| 7,033,823 B2 | 4/2006 | Chang | |
| 2002/0053915 A1* | 5/2002 | Weaver et al. | 324/600 |
| 2002/0173033 A1 | 11/2002 | Hammerick et al. | |
| 2003/0215941 A1 | 11/2003 | Campbell et al. | |
| 2004/0067546 A1 | 4/2004 | Leng et al. | |
| 2004/0084370 A1 | 5/2004 | Singh et al. | |
| 2004/0152067 A1 | 8/2004 | Wang et al. | |
| 2004/0219184 A1 | 11/2004 | Brown et al. | |
| 2005/0202096 A1 | 9/2005 | Li et al. | |
| 2006/0286661 A1* | 12/2006 | Gu et al. | 435/287.1 |

FOREIGN PATENT DOCUMENTS

| | | |
|---|---|---|
| EP | 1064353 B1 | 1/2001 |
| WO | WO 2005/108547 | 11/2005 |

OTHER PUBLICATIONS

Andersson, T. et al., "Frog melanophores cultured on fluorescent microbeads: biomimic-based biosensing," *Biosensors and Bioelectronics* 2005, 21, 111-120.

(Continued)

*Primary Examiner* — Walter D Griffin
*Assistant Examiner* — Lydia Edwards
(74) *Attorney, Agent, or Firm* — Wolf, Greenfield & Sacks, P.C.

(57) ABSTRACT

The present invention relates to articles and methods involving porous materials (e.g., membranes) which may interact with species, such as biological molecules, cells, etc., whereby the species may adhere to or become immobilized with respect to a surface of the porous material or an adhesion layer coating the porous surface. The porous material may be capable of attaching species with control over the positioning and spatial distribution of the species across the surface of the material. Such articles and methods may be useful in, for example, biological assays, biological sensors, or in the culturing of biological cells.

18 Claims, 6 Drawing Sheets

OTHER PUBLICATIONS

Assefa, Z. et al., "Ultraviolet radiation-induced apoptosis in keratinocytes: On the role of cytosolic factors," *Biochimica et Biophysica Acta* 2005, 1755, 90-106.

Dehring, H. et l., "Automated robotic liquid handling/laser-based nephelometry system for high throughput measurement of kinetic aqueous solubility," *Journal of Pharmaceutical and Biomedical Analysis* 2004, 36, 447-456.

Gebhart, R. et al., "New hepatocyte in vitro systems for drug metabolism: metabolic capacity and recommendations for application in basic research and drug development, standard operation procedures," *Drug Metabolism Review* 2003, 35, 145-213.

Gopalakrishnan, R. et al., "A cell-based microarrayed compound screening format for identifying agonists of G-protein-coupled receptors," *Analytical Biochemistry* 2003, 321, 192-201.

Raghavan, S. et al., "Micropatterned Environments in Cell Biology," *Adv. Mater.* 2004, 16(15), 1303-1313.

Tan, J. L. et al., "Simple Approach to Micropattern Cells on Common Culture Substrates by Tuning Substrate Wettability," *Tissue Engineering* 2004, 10, 865-872.

Viravaidya, A. et al., "Development of a microscale cell culture analog to probe naphthalene toxicity," *Biotechnology Progress* 2004, 20, 316-323.

International Search Report and Written Opinion, from PCT/US2006/049082, mailed Jul. 19, 2007.

International Preliminary Report on Patentability, from PCT/US2006/049082, mailed Mar. 25, 2008.

European Office Action from EP 06 849 257.8-2401, mailed Nov. 17, 2008.

European Office Action from EP 06 849 257.8-2401, mailed Oct. 9, 2009.

Ma, S., et al., "An endothelial and astrocyte co-culture model of the blood-brain barrier utilizing an ultra-thin, nanofabricated silicon nitride membrane", Lab on a Chip, Jan. 2005, vol. 5, No. 1, pp. 74-85.

Office Action from European Application No. 06 849 257.8-2401, mailed Jul. 29, 2010.

Office Action from European Application No. 06 849 257.8-2401, mailed Dec. 8, 2010.

* cited by examiner a)

HIGH THROUGHPUT CELL-BASED ASSAYS FABRICATED WITH INTEGRATED SILICON AND CELL CULTURE TECHNOLOGIES

FIELD OF THE INVENTION

The present invention relates to articles and methods for use in the study of biological molecules and/or biological cells.

BACKGROUND OF THE INVENTION

Cell-based devices have been used in many high-throughput pharmaceuticals testing systems to study cell behavior, including cell growth, cell migration, and cellular response to agents such as toxins, pathogens, drugs, or other cells. The use of materials such as membranes within cell culture environment has furthered the development of cell-based devices that may find use in various applications. Many systems employ the use of polymer membranes, wherein cells may adhere to the surface of the membrane or within the pores of the membrane, and their behavior may be studied. For many known polymeric membranes, both pore size and pore distribution may be difficult to control, limiting the ability to accurately monitor cell behavior. One method of achieving greater control of pore size and distribution may be to utilize multiple layers of polymeric membranes, resulting in composite membranes having increased thickness (e.g., at least 40 microns) and decreased flexibility. This may be detrimental to studies involving, for example, interaction between cells on opposite sides of the composite membrane. Conversely, polymeric membranes having decreased thickness often are characterized by undesirably poor mechanical strength. Additionally, it may be difficult to control and monitor the adherence of cells to many conventional polymeric membranes. While cells may adhere to the pores, they may also adhere to locations in between pores, which may prevent the growth ordered tissue, or otherwise be undesirable for certain applications.

Accordingly, improved methods and materials are needed.

SUMMARY OF THE INVENTION

The present invention, in certain embodiments, relates to apparatuses configured for cell culturing and/or cell assay comprising a membrane. The membrane may comprise an primarily an inorganic material and comprises a first side and a second, opposing side, and a plurality of pores spanning the membrane from the first side to the second side.

The present invention also relates to articles for cell culturing and/or cell assay comprising a membrane having a first side and a second, opposing side; a plurality of pores spanning the membrane from the first side to the second side and a cell adhesive material layer positioned on the first side of the membrane such that the cell adhesive material layer is exposed through the pores to an environment in contact with the second, opposing side and occludes at least some of the plurality of pores.

In another aspect, the present invention provides methods comprising providing a membrane comprising a first side, a second, opposing side, and a plurality of pores spanning the membrane between the first and second sides; placing cells on the membrane, wherein the pores are sized such that the cells substantially seal the pores to substantially prevent fluid flow across the membrane between the first and second sides of the membrane; exposing the first side of the membrane to a first fluid and the second side of the membrane to a second fluid, wherein fluid exchange does not occur across the membrane between the first and second sides or occurs at a rate of less than 1 cm$^3$ fluid per hour per cm$^2$ membrane surface area.

The present invention also provides methods comprising providing a membrane having a first side and a second, opposing side and a plurality of pores spanning the membrane between the first and second sides; presenting cells to at least the first side of the membrane; and determining migration of at least one of these cells through the pores from the first side to the second side.

BRIEF DESCRIPTION OF THE DRAWINGS

The accompanying drawings are schematic are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention. In the drawings.

DETAILED DESCRIPTION

The present invention relates to articles and methods involving materials, which may be porous, especially membranes, which may be useful in various applications, particularly applications involving the culture of cells and/or assays involving cells. Certain materials (e.g., membranes or multi-component materials including membrane(s)) of the present invention may interact with species, such as biological molecules (which may be present on the surface of a cell), whereby the species may adhere to a surface of or become associated with the material. In some embodiments, a material of the invention may be capable of allowing control over the positioning and spatial distribution of the species across the surface of the material. Such materials and methods may be useful in, for example, biological assays, biological sensors, or in the culturing of biological cells.

Articles and apparatuses of the present invention may comprise membranes useful in the study of biological molecules and/or biological cells. Typical previously known systems for cell studies often employed membranes having a random spatial distribution of pores, as well as poor control over average pore size. The use of such materials in the study and use of species, such as cells, attached to the surface of the membrane may produce inconsistent and/or difficult to interpret results. In contrast, the present invention, in certain embodiments, provides membranes which may be fabricated with control over both pore size and the spatial distribution of pores. As a result, the immobilization of species, such as cells, with respect to the membrane may also be controlled, in some cases, based on the spatial distribution of the pores. For example, the pores of the membranes may direct the adhesion of species to a surface such that a substantial majority of the species adhere only in regions, within, coextensive with or overlapping pores, rather than the areas between pores. The spatial control of the adhered species may be advantageous in numerous applications. For example, the controlled adhesion of cells on a surface may be useful in tissue engineering, as described more fully below. Additionally, membranes of the present invention may be thin (e.g., less than 40 microns in thickness) and flexible relative to other, conventional membranes, which may facilitate contact between species on opposing sides of the membrane.

The present invention, in certain embodiments, provides articles comprising membranes for use in cell culturing and/or cell assays, such articles comprising a membrane having a first side and a second, opposing side and a plurality of pores spanning the membrane from the first side to the second side, wherein the membrane comprises primarily an inorganic material.

As used herein, the term "inorganic material" is given its ordinary meaning, meaning anything that is not an organic material. "Organic material" is also used according to its ordinary meaning in this context, namely, materials composed of molecules containing one or more carbon-hydrogen bond. For example, inorganic materials may include, but are not limited to, materials comprising at least one metal atom (e.g., metal atoms selected from Groups 1-17) and/or compounds thereof, wherein such compounds typically do not contain functional groups comprising carbon atoms bound to hydrogen. Some examples of inorganic materials may include ceramics, glasses, and metals. In some cases, the inorganic material comprises metal oxides or metal nitrides. In a particular embodiment, the inorganic material may be silicon nitride (SiN). The inorganic material may be opaque, semi-opaque translucent, or transparent, and may be gas permeable, semi-permeable or gas impermeable. In some cases, the inorganic material may be selected to be optically transparent at wavelengths greater than about 400 nm. The inorganic material may also be selected to be compatible with cells and/or biological molecules. A wide variety of suitable inorganic materials that may be utilized according to the invention will become readily apparent to or can be selected without undue experimentation by those of ordinary skill in the art given the guidance and teaching provided herein.

In some embodiments, membranes of the present invention may comprise a single layer of material (e.g., an inorganic material). In certain embodiments, the membrane may comprise at least one portion having a thickness measured between the first and second sides of less than about 30 microns. In some embodiments, the thickness may be less than about 20 microns, less than about 10 microns, or less than about 5 microns.

In some embodiments, the membrane is constructed to have a relatively homogeneous pore size distribution, for example such that no more than about 5% of all pores deviate in size from the average pore size by more than about 10%, in some cases, by no more than about 5%. "Pore size" as used herein may be determined microscopically, for example using either or both of visible light microscopy or scanning electron microscopy (SEM) and refers to the length of the shortest line parallel to a surface of the membrane connecting two points around the circumference of a pore and passing through the geometric center of the pore opening.

Using microfabrication techniques known to those of ordinary skill in the art, the cross-sectional shape (circular, oval, triangular, irregular, square or rectangular, or the like), number, and dimensions of the pores can be varied to suit a particular application. A variety of suitable or potentially suitable microfabrication techniques are discussed in, for example, *Silicon processing for the VLSI Era, $2^{nd}$ Ed.*, Vol. 1, S. Wolf and R. N. Tauber, Lattice Press, Sunset Beach, Calif. (2000); M. J. Bowden, "A Perspective on resist Materials for fine line lithography", in *Materials for Microlithography, Advances in chemistry Series,* # 266, American Chemical Society, Washington, D.C., Chap. 3, p. 39-117 (1984); D. Nyyssonen, "Optical Linewidth Measurement on Patterned Wafers," *SPIE proceedings*, Vol. 480, Integrated Circuit Metrology, p. 65 (1984); and J. D. Cuthbert, "Optical Projection Printing," *Solid State Technology*, P. 59, August 1977; each of which is incorporated by reference. For example, the pores may have an essentially circular cross-sectional profile. In some cases, the pores may have a smallest diameter that is smaller than a smallest cross-sectional dimension of a species to which the membrane may be exposed. In some cases, the pore size may be selected to be much larger than a species to which the membrane may be exposed. Furthermore, the spatial distribution of the pores may be controlled using known techniques, such that at least about 50% of the pores are positioned less than about 25 microns from a nearest, adjacent pore. In some embodiments, the pores may have an average pore size of about 0.2 microns to about 100 microns with a size deviation of no more than about 2-3%. In certain embodiments, the minimum pore size is at least about 1 micron. Typically, the spatial distribution of the pores may be such that the distance between nearest, adjacent pores may be about 1-50 microns. In each case, the above-referenced distances separating adjacent pores refers to the shortest distance connecting the peripheral circumference of a particular pore with the peripheral circumference of the nearest adjacent pore.

For embodiments where photolithography is used a technique for fabrication of an inventive membrane, the pore sizes may be determined by the design/drawn feature size of the particular lithography masks utilized. Pore spacing may be determined by a combination of materials used and lithography tools employed. For fabrication of membranes that possess advantageous mechanical stability, pore spacing may be such that the distance between nearest, adjacent pores may be about 2 microns or more. The thickness of the membrane can be widely varied, for example from about 200 nm to about 2 microns depending on the thickness of the thin film deposited on the substrate material.

In some embodiments, the membrane, as coated with a cell adhesive layer and cells for certain embodiments, may include at least one portion, having an area of at least about 1 $mm^2$, which exhibits at least 30% transmission of light at at least one wavelength within a wavelength range from about 400 nm to about 800 nm; in other embodiments, at least 40% or at least 50% transmission of light at at least one wavelength within a wavelength range of from 400 nm to about 800 nm in such portion(s). In one embodiment, a SiN membrane may be capable of blocking transmission of UV light, which may be advantageous in, for example, environmental sensing systems since UV light may cause cell membrane denaturation and cell death. This may simplify the construction of such devices, since UV light may be inherently filtered from the system by the membrane.

Figure 2A:
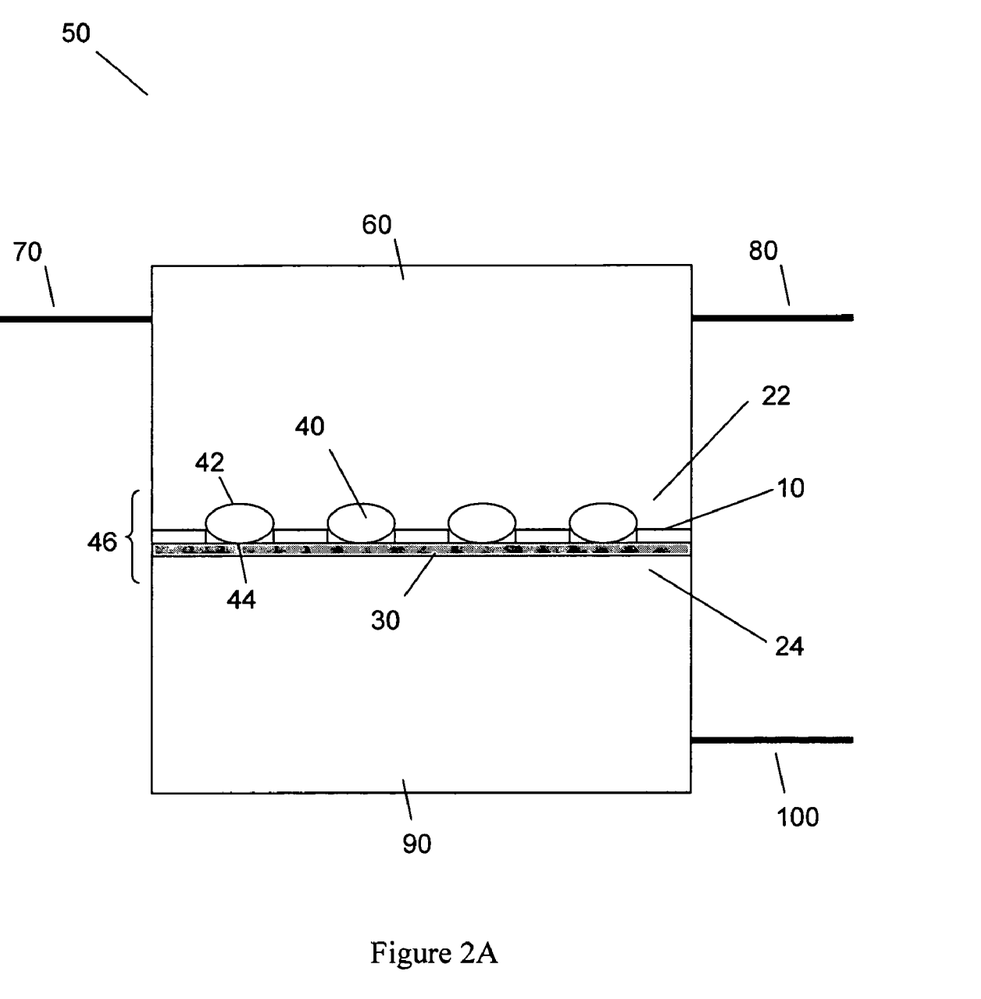
FIG. 2A illustrates, schematically, a two-chamber system according to one embodiment of the invention.
Figure 2B:
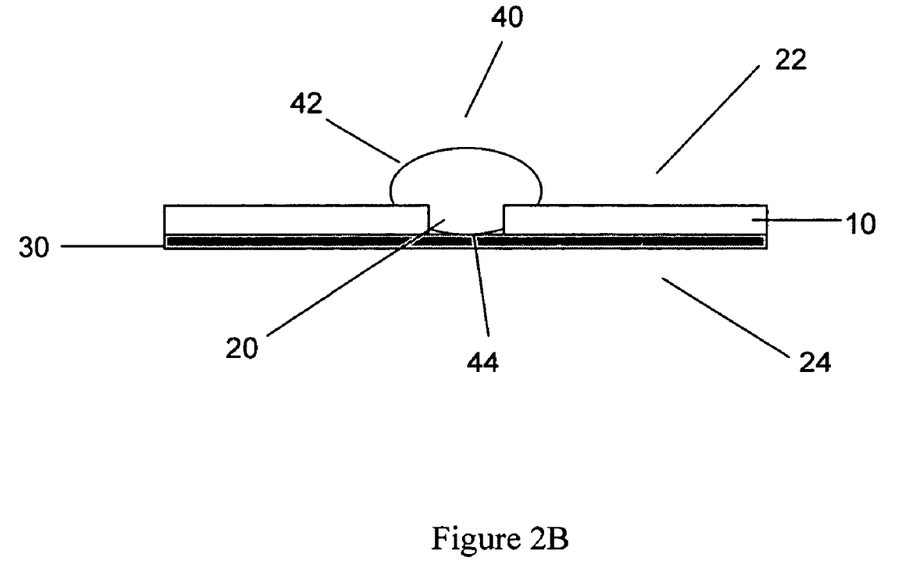
FIG. 2B illustrates a cell adhered to a pore within a membrane, according to one embodiment of the invention.

Membranes of the invention may also be capable of or modified to permit the adhering of various species to the surface of the membrane or to a material coating a surface of the membrane. For example, cells and/or biological molecules such as proteins, and the like may become immobilized with respect to various portions of the membrane, including, for example, areas along the side walls of the pores or areas between the pores on a surface of the membrane. In some embodiments, such species may preferentially adhere to certain areas of the membrane rather than other areas. For example, substantially all such species may adhere within regions coextensive with, within or overlapping the pores of the membrane rather than in areas between the pores. The pores may be sized such that, when a species is adhered within a region coextensive with, within or overlapping a pore, at least a portion of the species is attached to a material attached to or associated with the membrane spanning the cross-sectional area of the pore in a plane parallel to a face of a side of the membrane. In some cases, the species may only adhere within a region coextensive with such a cross-sectional area of the pore. In some cases, the species may adhere to a region coextensive with a substantial majority of such cross-sectional area of the pore such that the species, e.g. a cell, substantially seals the pore, as described further below and as illustrated in FIG. 2B.

Some articles of the invention may comprise an adhesive material selected to preferentially attract and/or bind a particular species, such as a cell or other biological species that is attached to, imobilized with respect to, or otherwise associated with at least one side of a membrane. For example, a membrane may comprise a cell adhesive material positioned on one surface of a side of the membrane such that, when the other side of the membrane is exposed to a medium containing cells, the cells may adhere to the regions comprising the cell adhesive material, exposed to the cells by being contained within and/or being present in a layer spanning and, in certain cases occluding, at least one pore of the membrane (e.g. see FIG. 1). In certain embodiments, the adhesive material is a cell adhesive material. The term "cell adhesive material" as used herein may refer to any chemical or biological material to which a cell may adhere. In certain embodiments, such a cell adhesive material is configured as a continuous layer attached to a surface of at least one side of a membrane. Such a cell adhesive material layer may comprise, any of a wide variety of species known in the art to be capable of binding to, specifically or non-specifically, membranes of biological cells or components thereof, such as for example, collagen or mixtures of collagen with polysaccharide, antibodies, ligands to cell surface receptors, antigens, lectins, integrins, selecting, bacterial derived affinity molecules such as Protein A or Protein G, derivatives thereof, mixtures thereof, any of the above associated with a gel or other layer-forming material, such as collagen, gelatin, agarose, acrylamide, chitosan, cellulose, dextran, an alginate, a carrageenan, etc., and the like.

Figure 1:
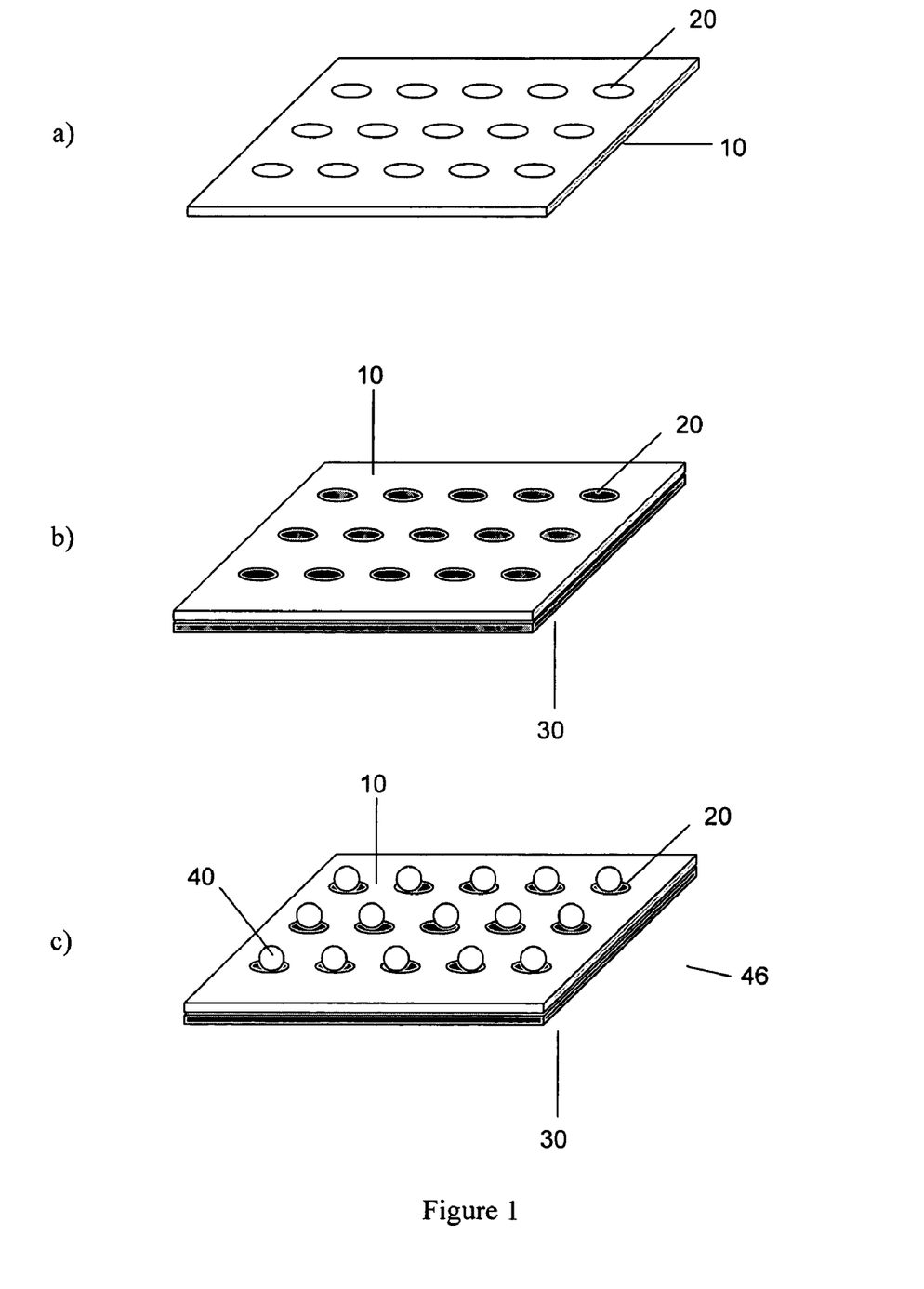
FIG. 1 illustrates, schematically, a cell-based device according to one embodiment of the invention.

In one embodiment, a cell adhesive material layer may be positioned on a first side of the membrane such that the cell adhesive material layer may be exposed through the pores to the second, opposing side of the membrane (i.e. to an environment in contact with the second side of the membrane). FIG. 1 shows one example of such an embodiment of the invention. FIG. 1a shows a membrane 10 comprising a plurality of pores 20. An adhesive material layer 30 may be formed and positioned on a first side of the membrane such that the material layer may be exposed in regions coextensive to the pores to a second, opposing side of the membrane (FIG. 1b). Exposure of the second side of the membrane to a cell 40 may result in adhesion of cell 40 to the exposed adhesive material 30 to form composite article 46. The adhesive material may be selected to preferentially bind a particular target species, such as a cell or a cell-surface associated species (e.g. a receptor, immunoglobin, etc.). Inventive systems such as illustrated in FIG. 1c can allow cells to be tested while adhered to a surface and may be useful in the study of cell behavior since the viability of many cell types may be dependent on cell adhesion. For example, cells adhered to, for example, collagen, may maintain their differentiated state for prolonged periods of incubation.

In other embodiments, the cell adhesive material may be positioned on or along any portion of the membrane. For example, the cell adhesive material layer may be positioned along sidewalls of the pores to achieve adhesion of cells within pores. The cell adhesive material layer may also be positioned only at the surface of a pore opening. Alternatively the cell adhesive material layer may be positioned only on the surface of the membrane between pores. The layer may be positioned in a single location on the membrane or a combination of locations on the membrane. Those of ordinary skill in the art would be able to select the positioning of the cell adhesive material layer to suit a particular application.

In some cases, the pores may be sized to allow only a single cell to adhere to, within, or in a region coextensive with a single pore, thereby allowing a plurality of physically isolated single cells to be arrayed over a surface of the membrane, wherein the spatial distribution of cells on the surface correlates to the spatial distribution of the pores. This may be advantageous in comparison to many conventional systems wherein cells may indiscriminately adhere to various locations on the surface of a membrane. In some cases, in use, at least 50% of the pores may attach a single cell to each pore. In some cases, at least 60%, at least 70%, or at least 80%.

Articles of the present invention may be incorporated into devices configured for the study of cells and/or other biological entities. For example, in certain embodiments, membranes as described herein may be used in a multi-chamber apparatus, wherein the apparatus comprises at least a first compartment and a second compartment constructed and arranged to contain, for example, fluid, such that the first and second compartments are be separated by the membrane. That is, the device may contain at least one compartment, wherein the compartment is enclosed by walls, wherein at least one wall comprises a membrane. The compartment may be capable of containing an environment, such as a fluid environment, to which the membrane may be exposed. The apparatus may further comprise components constructed and arranged to facilitate containment, within each compartment, of a fluid positioned adjacent the membrane. For example, the apparatus may comprise various inlets, outlets, pumps, and the like, which may allow for the positioning of a fluid in contact with the membrane. FIG. 2A shows an illustrative example of such an embodiment of the invention. A composite layer 46 comprising a membrane 10 and a cell adhesive material 30 and adhered cells 40 as described previously is be positioned in device 50 such that the layer separates chamber 60 from chamber 90. Channels 70, 80, and 100 may be used to introduce fluid and/or other components into the device or remove fluid and/or other components from the device. A cell 40 may adhere over or within a pore 20 such that a top portion 42 and a bottom portion 44 of cell 40 may each be exposed to the different environments present on opposing sides of the membrane. Top portion 42 of the cell may be exposed to one environment in contact with a top surface 22 of the membrane, while bottom portion 44 of the cell may be exposed to another environment in contact with a bottom surface 24 of the membrane and/or the cell adhesive material.

In some embodiments, devices of the invention comprising membranes may be configured to allow for the monitoring of and controlled growth of tissue. Unlike certain conventional platforms for tissue growth and engineering that are unable to control important aspects of the adhesion of cells to the surface of a matrix, resulting in poorly ordered tissue formation, certain platforms provided by certain embodiments of the present invention, having a defined architecture for guiding cell growth, may facilitate the generation of highly ordered and physiologically correct tissue. Also, such inventive materials may aid in the study of factors and conditions which influence the growth and development of tissue. In some embodiments, articles comprising membranes of the invention may have the ability to form an ordered array of adhered cells on a surface, which may facilitate the directional growth of cells and tissue.

The ability to control the spacing of adhered cells on a surface may be particularly useful in various applications for studying the response of a cell to a biological agent and/or molecule and/or individual cell responses or cell-cell signaling or other cell-cell interactions. In some embodiments, the membrane may comprise an ordered array of adhered cells, i.e., wherein single cells may be attached to regions coextensive with single pores across the surface of the membrane, allowing, in certain cases, for the rapid screening of the effects of exposure of cells to biological molecules and/or biological agents upon exposure of at least one side of the membrane to the biological molecule and/or agent. In some embodiments, a first set of cells may be adhered to the surface of a membrane and may be exposed, on at least one side of the membrane, to an environment comprising a second set of cells, such as cancer cells. The cell-to-cell interaction the first set of cells (e.g., the adhered cells) and the second set of cells may be monitored, in some cases, at a particular portion of the adhered cell. Certain membranes of the invention may be particularly useful for the study of cell-to-cell interactions since the membranes may be sufficiently thin (e.g., less than 40 microns thick) to allow for cells on opposing sides of the membrane to contact one another through pores.

Cells adhered to articles comprising a membrane of the invention may also be exposed to other biological molecules and/or agents (e.g., proteins, antibodies, and the like) to, for example, screen the efficacy and/or cytotoxicity of, for example, antibodies, antigens, growth and regulatory factors, or the like on the cells or certain functions thereof. Additionally, cellular behavior, mechanisms, and processes may also be studied. For example, exposure of bottom surface 24 of an article comprising a membrane to an environment comprising a biological agent may allow for the study of the cellular response to the biological agent, in some cases, specifically at bottom portion 44 of the cell (FIG. 2B).

As described above, in some cases, articles of the invention may be incorporated into multi-chamber perfusion systems, for example, for cell culturing. FIG. 2A shows an illustrative embodiment of the invention configured for such an application. A article 46 comprising a membrane coated with a cell adhesive material layer as described herein is positioned in device 50 such that the article separates chamber 60 from chamber 90. Channel 70 may be used to introduce fluid and/or other components into chamber 60 such that the fluid and/or other components contact top surface 22 of the article. Channel 100 may be used to introduce and/or remove fluid and/or other components into or from chamber 90 such that the fluid and/or other components contact bottom surface 24 of the article.

In some embodiments, fluid exchange through the membrane may be substantially prevented by the presence of the cell adhesive layer 30 and/or cells 40. For example, fluid exchange may not occur through the membrane between the first and second sides of the membrane or may occur at a rate of less than 1 cm$^3$ fluid per hour per cm$^2$ membrane surface area. In the illustrative embodiment shown in FIG. 2A, the membrane/cell adhesive layer/attached cell composite may prevent substantial fluid exchange between chamber 60 and chamber 90.

Some embodiments may comprise cells positioned on a membrane, wherein the pores are sized such that the cells are able, when they become immobilized to a region coextensive with, within or overlapping a pore, to substantially seal such pore. For example, the pore may have a size that may be sufficiently small as to become covered and/or sealed by an adhered cell, wherein at least portion of the cell may adhere to a substantial majority of the a region co-extensive with a cross-sectional area of the pore taken in a plane parallel to a surface (e.g. surface 22) of the membrane.

As shown in FIG. 2B, cell 40 may adhere to cell adhesive layer 30 in the region of pore 20 such that pore 20 may be substantially sealed to prevent, for example, fluid exchange or diffusion between opposing sides of the membrane, except as may occur through cell 40 itself. In some cases, the cell may only permit the exchange of certain species across the membrane via interaction with the cell (e.g. diffusion and/or active transport across/through the cell). For example, one side of the membrane may be exposed to an environment comprising species which may promote cell survival and growth, which the cell may absorb through the cell membrane. Similarly, the cell may also excrete various species via the cell membrane into the other chamber. In one illustrative embodiment, cell 40 may comprise a top portion 42 (e.g., an apical membrane) and a bottom portion 44 (e.g., a basal membrane) such that, when adhered to cell adhesive layer 30 in the region of pore 20, the top portion 42 and the bottom portion 44 may be exposed to different fluidic environments in a two-chamber system (such as illustrated in FIG. 2A). In one such embodiment, channel 70 may be used to carry oxygen, nitrogen, carbon dioxide, nutrients, culture media or the like into chamber 60 one or more of which may be transported into the cell through cell portion 42 of the cell (e.g., the apical membrane). Waste products may then be secreted by cell portion 44 (e.g., the basal membrane) away from the cells into chamber 90. Channel 100 may be used to transport the waste products out of device 50. Thus, a high cell viability may be maintainable through long periods of cell culture.

Another aspect of the present invention provides a method for studying cell migration. Cell migration may be important in the study of, for example, wound healing, tissue formation (e.g., repair, development, such as embryonic development, and the like), disease progression (e.g., cancer progression), and/or immune responses, which may require movement of cells in a particular direction to a specific location. For example, the initial phase of wound healing (e.g., cutaneous or vascular wound healing) may involve cell migration into the wounded area rather than cell division to replace the lost or injured cells. The inventive method may comprise presenting cells to a first side of a membrane as described herein and determining migration of the cells through the pores from the first side of the membrane to the second side of the membrane. In some, embodiments, the method may comprise adhering cells to a surface of the membrane and determining migration of the cells across the surface, for example, between at least two pores. The migration of cells may be determined by methods known to those of ordinary skill in the art. In one example, cells may enter the pores from a first side of the membrane, and the cell migration may be monitored by measuring the number of cells which exit the pores from a second side of the membrane.

In some cases, membranes of the invention may comprise a cell migration inducing or inhibiting agent, A "cell migration agent" may be any chemical or biological species that may promote or inhibit the migration of cells across an area, for example, into a wound area. Cell migration agents may be one or more of polynucleotides, proteins, sugars, lipids, organic molecules, synthetic or natural pharmaceutical agents, an/d or other cell migration agents know to those of ordinary skill in the art. Membranes of the invention used for cell migration studies may comprise cell migration agents positioned along, and optionally attached to, the side walls of the pores, the entrance of the pores, the surface of one or more sides of the membrane, or any other portion or portions of the membrane. In some cases, the size of the pores may be sufficiently large to facilitate the entry of cells within the pores and/or migration of cells through the pores.

Membranes of the invention may, in certain embodiments, primarily comprise, or in certain embodiments consist essentially of, or in other embodiments consist of, an inorganic material. The inorganic material may be for example, any suitable metal oxide(s) and/or metal nitride(s). In some cases, the inorganic material comprises SiN, $SiO_2$, $Al_2O_3$, $TiO_2$, and/or TiN. In a particular embodiment, the inorganic material comprises SiN. As previously discussed, the inorganic material may be selected to suit a particular application. For example, the inorganic material may be selected based on its biocompatibility with cells, i.e., the inorganic material may be substantially non-toxic. In some cases, the inorganic material may exhibit at least 30% transmission of light at at least one wavelength within a wavelength range of from about 400 to about 800 nm.

The membranes may be formed using any of a variety of suitable microfabrication techniques known in the art, as previously discussed. For example, micro-stamping, photolithography, etching, stenciling, or other silicon microfabrication techniques, and the like. In certain embodiments, for example certain embodiments where the membranes are utilized in an apparatus configured for cell culture and/or cell assays, membranes may be advantageously formed using photolithography techniques. In some embodiments, the membrane or membrane precursor may be nitridated by methods known in the art in order to form a metal nitride layer. For example, a nitride film may be formed on a silicon wafer upon exposure to a nitrogen environment (e.g, ammonia, and the like) or by any chemical and/or physical deposition processes, such as chemical vapor deposition, pulsed laser deposition, vacuum plasma spray, wet spray, sputtering, evaporation, molecular beam epitaxy, or the like.

In some embodiments, a biological species may be adhered to the membrane and/or to an adhesive layer attached to or otherwise immobilized with respect to or associated with the membrane. The biological species may include cells, or biological molecules such as proteins and peptides, antibodies, and the like. In some embodiments, the biological species may be a cell, such as a mammalian cell or a bacterial cell. In some cases, hepatocytes or anchorage-dependent cells or cell lines may be studied.

The function and advantage of these and other embodiments of the present invention may be more fully understood from the examples below. The following examples, while illustrative of certain embodiments of the invention, do not exemplify the full scope of the invention.

EXAMPLES

Example 1

Silicon nitride membranes with pores ranging in size from about 3 microns to about 30 microns (measured via SEM) and pore spacing ranging from about 3 microns to about 18 microns were microfabricated using known techniques as described below. Four-inch silicon <100> wafers were first cleaned using Radio Corporation of America (RCA) cleaning technique and spun dry in nitrogen to remove any contaminants that may be present on the surface of the silicon wafers. Next, a layer of low-stress nitride (1 μm) was grown at 800° C. at 200 mtorr in ambient gas flows of dichlorosilane and ammonia (at 95 sccm and 16 sccm, respectively). The measured stress of the deposited silicon nitride film was tensile in nature (180 MPa). The silicon nitride film thickness was measured with a Filmetrics interferometer, and the average film thickness varied by less than 2% for all wafers. Pores on the nitride membrane were patterned on the front-side of the wafers by first spinning AZ7220 photoresist on the wafers. Next, the photoresist was exposed, through a chrome mask, with an EVG620 contact aligner, and the exposed wafers were developed with Shipeley's MIF-300 developer. After the wafers were hard-baked, the silicon nitride film was etched with an Alcatel inductive coupled plasma etcher with 10 sccm of $O_2$ and 100 sccm of $CHF_3$, at a pressure of 50 mTorr. Using the same lithography and etch processes, backside etch windows were patterned. The photoresists were stripped in an ultrasonic bath of N-methylpyrrolidone (NMP) at 80° C. Finally, the wafers were rinsed with deionized water, and spun dry. The pores on the silicon nitride membranes were exposed by placing the wafers in a single-side etch holder for wet-etching. The membranes were etched in 25% tetramethylammonium hydroxide (TMAH) at 90° C. Finally, the wafers were rinsed in deionized water and methanol, and air dried. The membrane used below in Example 4 for cell patterning had a relatively homogeneous pore size distribution with pores having a pore size of about 18 microns, and a pore spacing of about 8 microns.

Example 2

A cell adhesion layer of collagen was formed by contacting a collagen solution (sterile solution of Type 1, pepsin-solubilized bovine dermal collagen at 1.5% wt. in 0.012N HCl (Vitrogen® Collagen In Solution, Nutacon BV, Netherlands)) with one side of the microfabricated porous silicon nitride membrane fabricated as described in Example 1. Contact angles of water and collagen solution on the fabricated silicon nitride surface were 49.2° and 48.4°, respectively. The hydrophilic surface allowed the collagen solution to spread uniformly over the nitride membrane and gel as a uniform layer on the membrane surface.

Example 3

Figure 3:
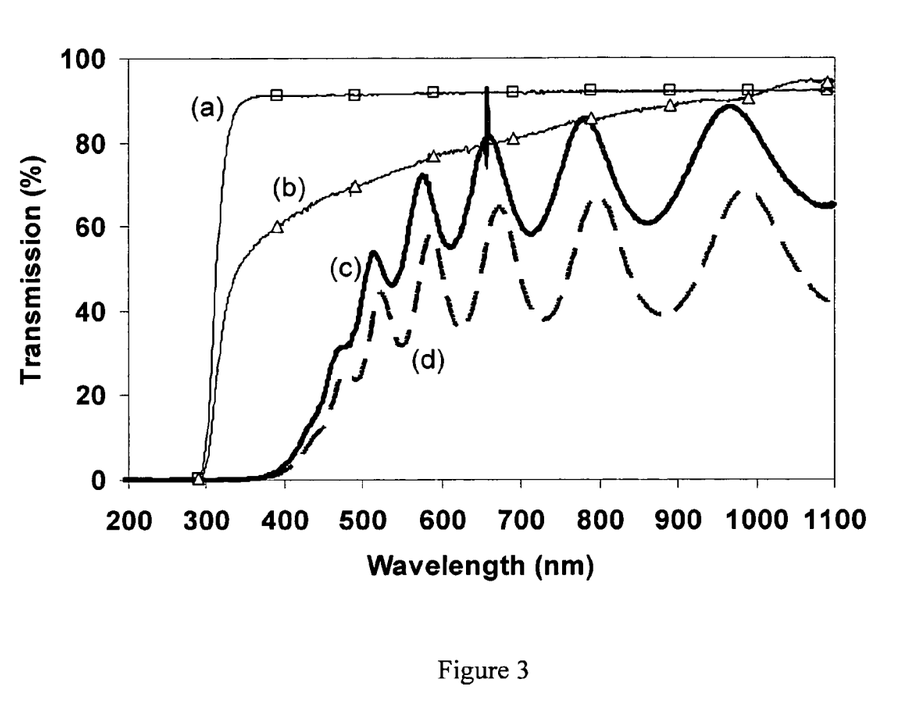
FIG. 3 shows the transmission spectra of light through (a) a glass substrate, (b) a glass substrate with collagen, (c) a silicon nitride membrane, and (d) a silicon nitride membrane with collagen and cells adhered to the collagen.

The light transmission through an unpatterned silicon nitride membrane was measured with an Agilent 8453 UV-visible spectrophotometer. FIG. 3 shows the transmission of light through (a) glass (curve A), (b) collagen-coated/glass (curve B), (c) silicon nitride membrane (curve C), (d) cells adhered to a collagen gel layer-coated silicon nitride membrane (curve D). Due to interference of light within the silicon nitride thin film, light transmission oscillated with wavelength changes. Light transmission through a stack containing cells/collagen/unpatterned silicon nitride membrane was only slightly lower than that through the unpatterned silicon nitride membrane. Thus, light absorption due to the presence of cells and collagen was not significant. However, due to the greater thickness of the stack, a phase shift in the oscillation was observed. Transmission of light through the cell layer/collagen/silicon nitride membrane was found to be more than 50% for wavelengths of 500-1000 nm, demonstrating that this platform could be used to assess and monitor cells non-invasively with standard fluorescence techniques.

Example 4

Silicon nitride membranes fabricated as described in Example 1 were coated with collagen on one side, and cells were adhered to the coated membrane, as shown schematically in FIG. 1. The patterned silicon nitride membranes were prepared for cell culture by first autoclaving the membranes at 120° C. for 1 h. Next, 40 µl of 1.5 mg/ml collagen solution at 4° C. was pipetted onto the back of the membrane. The collagen was allowed to gel at 37° C. in an $O_2$ incubator for 1 h. Subsequently, the membranes were turned and covered with 50 µl of primary hepatocyte cell suspension ($10^5$ cells/ml). The cells were seeded onto the exposed collagen for 45 min in Hepatozyme SFM culture media (Gibco Laboratories, California). The membranes were then washed in culture medium, and placed into a 12-well plate, filled with 2 ml of culture medium.

Figure 4:
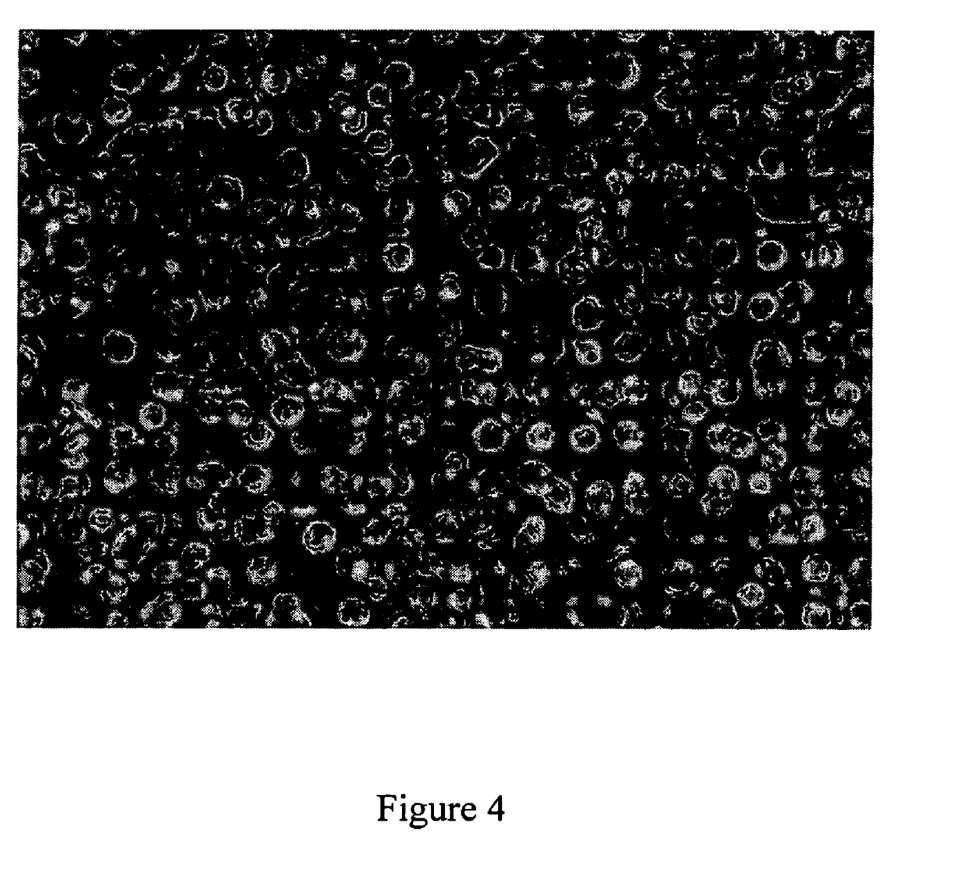
FIG. 4 shows an optical micrograph of cells seeded onto a porous silicon nitride membrane coated with collagen.

Due to the micropatterned surface of the membrane, a large number of cells could be positioned onto the silicon nitride membrane in a single step. To demonstrate this technique, an array of pores (1 mm×1 mm array of pores with an average pore size of about 18 microns) with collagen coated on the backside of membrane was exposed to a cell suspension on the front side of the membrane. The cells were allowed to adhere onto the exposed collagen for 4 h. An optical micrograph of the front side of the membrane, where the cells seeded onto the porous silicon nitride membrane, shows that the cells positioned themselves over the pores (FIG. 4). About 80% of the pores were observed to covered by one single cell/pore. Larger cells that were in contact with their neighbors were adhered to each other, forming chains of cells. After 5 days of culturing, the hepatocytes remained immobilized to the collagen layer coating the silicon nitride membrane. These results show that this technique could be used to develop a high-throughput process of creating many single-cell biosensors.

Example 5

Figure 5:
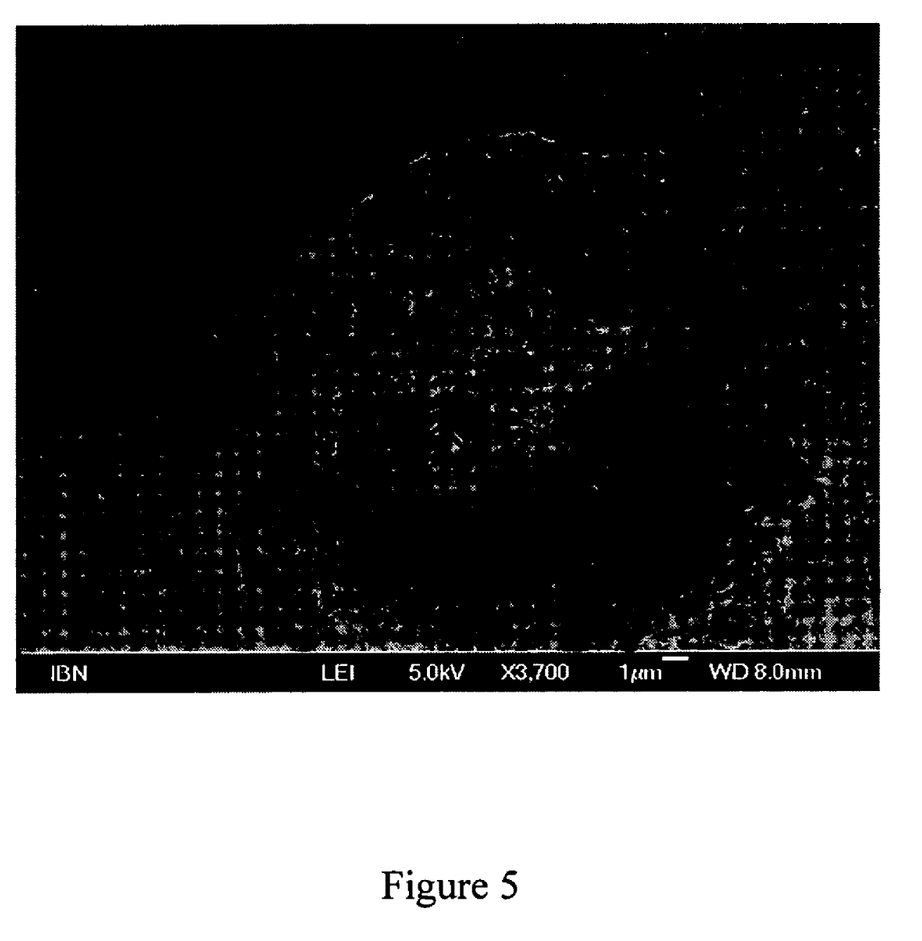
FIG. 5 shows an SEM micrograph of a single cell positioned on top of a microfabricated pore coated with collagen gel from the backside of a silicon nitride membrane.

The membrane with adhered cells prepared according to the process described in Example 4 was then studied using scanning electron microscopy (SEM). The SEM sample was prepared by first fixing the cells (immobilized with respect to the membrane) overnight in 2% glutaraldehyde. Next, the cells were dehydrated by subsequent immersions in a series of ethanolic solution of increasing concentration (30% to 100% in steps of 10%). The membrane with cells was then dried using a Tousimis critical point drier, and platinum was sputtered onto the sample surface. The SEM micrograph in FIG. 5 shows a single cell positioned on top of a microfabricated pore coated with collagen gel on the backside of the silicon nitride membrane. The collagen gel did not permeate through the pores to the front-side of the silicon nitride membrane, allowing accurate positioning of a single cell over/within the pore.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, materials, reaction conditions, and configurations described herein are meant to be exemplary and that actual parameters, materials, reaction conditions, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood, unless otherwise indicated, to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

All references cited herein, including patents and published applications, are incorporated herein by reference. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed:

1. An apparatus comprising:
   a membrane, the membrane comprising:
   a first side;
   a second, opposing side;
   a plurality of pores spanning the membrane from the first side to the second side;
   a cell adhesive material layer positioned on the first side of the membrane, with the second side of the membrane remaining essentially free of the cell adhesive material; and
   cells positioned on the second side of the membrane and attached to the cell adhesive material layer through the pores,
   wherein the membrane comprises primarily inorganic material, and
   wherein at least about 50% of the pores are positioned less than about 25 microns from a nearest, adjacent pore and the apparatus is configured for cell culturing and/or performing a cell assay.

2. An apparatus as in claim 1, further comprising:
   first and second compartments constructed and arranged to contain fluid, the first and second compartments separated by the membrane; and
   components constructed and arranged to facilitate containment, within each compartment, of a fluid positioned adjacent the membrane.

3. An apparatus as in claim 1, wherein the cell adhesive material layer occludes at least some of the plurality of pores.

4. An apparatus as in claim 3, wherein the cell adhesive material layer occludes essentially all of the plurality of pores.

5. An apparatus as in claim 1, wherein the cell adhesive material layer comprises collagen.

6. An apparatus as in claim 1, wherein the inorganic material is a metal oxide and/or metal nitride.

7. An apparatus as in claim 6, wherein the inorganic material is silicon nitride.

8. An apparatus as in claim 1, wherein the membrane comprises at least one portion having a thickness measured between the first and second sides of less than about 30 microns.

9. An apparatus as in claim 8, wherein the membrane comprises at least one portion having a thickness measured between the first and second sides of less than about 20 microns.

10. An apparatus as in claim 9, wherein the membrane comprises at least one portion having a thickness measured between the first and second sides of less than about 10 microns.

11. An apparatus as in claim 10, wherein the membrane comprises at least one portion having a thickness measured between the first and second sides of less than about 5 microns.

12. An apparatus as in claim 1, wherein no more than about 5% of all pores deviate in size from an average pore size of the plurality of pores by more than about 10%.

13. An apparatus as in claim 1, wherein no more than about 5% of all pores deviate in size from an average pore size of the plurality of pores by more than about 5%.

14. An apparatus as in claim 1, wherein the membrane includes at least one portion, having an area of at least about 1 mm$^2$, which exhibits at least 30% transmission of light at least one wavelength within a wavelength range of from about 400 nm to about 800 nm.

15. An apparatus as in claim 14, wherein the membrane includes at least one portion, having an area of at least about 1 mm$^2$, which exhibits at least 40% transmission of light at least one wavelength within a wavelength range of from about 400 nm to about 800 nm.

16. An apparatus as in claim 15, wherein the membrane includes at least one portion, having an area of at least about 1 mm$^2$, which exhibits at least 50% transmission of light at least one wavelength within a wavelength range of from about 400 nm to about 800 nm.

17. An apparatus as in claim 1, wherein each attached cell is associated with a single pore, such that a spatial distribution of the cells on the membrane is directed by a spatial distribution of the pores.

18. An article for cell culturing and/or cell assay, comprising:
   a membrane having a first side and a second, opposing side;
   a plurality of pores spanning the membrane from the first side to the second side;
   a cell adhesive material layer positioned on the first side of the membrane such that the cell adhesive material layer is exposed through the pores to an environment in contact with the second, opposing side and occludes at least some of the plurality of pores; and
   cells positioned on the second side of the membrane and attached to the cell adhesive material layer, wherein each attached cell is associated with a single pore, such that a spatial distribution of the cells on the membrane is directed by a spatial distribution of the pores.

* * * * *

UNITED STATES PATENT AND TRADEMARK OFFICE
CERTIFICATE OF CORRECTION

PATENT NO.        : 8,003,380 B2
APPLICATION NO.   : 11/325609
DATED             : August 23, 2011
INVENTOR(S)       : Shyi Herng Kan et al.

It is certified that error appears in the above-identified patent and that said Letters Patent is hereby corrected as shown below:

Column 5, line 23, "imobilized" should be "immobilized"

Column 5, lines 43-44, "selecting" should be "selectins"

Column 14, Claim 14, line 25, "transmission of light at" should be "transmission of light at at"

Column 14, Claim 15, line 30, "transmission of light at" should be "transmission of light at at"

Column 14, Claim 16, line 35, "transmission of light at" should be "transmission of light at at"

Signed and Sealed this
Twenty-ninth Day of November, 2011

David J. Kappos
*Director of the United States Patent and Trademark Office*